United States Patent [19]

Lindow et al.

[11] Patent Number: 4,689,491

[45] Date of Patent: Aug. 25, 1987

[54] SEMICONDUCTOR WAFER SCANNING SYSTEM

[75] Inventors: James T. Lindow, Saratoga; Simon D. Bennett; Ian R. Smith, both of Los Gatos; Gary A. Melmon, Saratoga, all of Calif.

[73] Assignee: Datasonics Corp., Campbell, Calif.

[21] Appl. No.: 725,082

[22] Filed: Apr. 19, 1985

[51] Int. Cl.$^4$ .................................... G01N 21/88
[52] U.S. Cl. .................................... 250/572; 356/445
[58] Field of Search ............... 250/571, 572; 356/244, 356/445, 371; 350/507, 508

[56] References Cited

U.S. PATENT DOCUMENTS

| T102,104 | 8/1982 | Kirk et al. | 356/387 |
|---|---|---|---|
| 3,836,787 | 9/1974 | Ash | 250/572 |
| 4,112,309 | 9/1978 | Nakazawa et al. | 250/560 |
| 4,194,127 | 3/1980 | Schmidt | 250/572 |
| 4,505,585 | 3/1985 | Yoshikawa et al. | 356/237 |

OTHER PUBLICATIONS

Marsman et al., "Mechanical Scan System for Microscopic Applications", Rev. Sci. Instrum., vol. 54, No. 8, pp. 1047–1052, Aug. 1983.
Brakenhoff et al., "Confocal Scanning Light Microscopy with High Aperture Immersion Lenses", J. Microsc., vol. 117, pp. 219–232, (1979).
Brakenhoff, "Imaging Modes in Confocal Scanning Light Microscopy (CSLM)", J. Microsc., vol. 117, pp. 233–242, (1979).

Primary Examiner—Eugene R. LaRoche
Assistant Examiner—Robert J. Pascal
Attorney, Agent, or Firm—Robert S. Kelly

[57] ABSTRACT

A semiconductor wafer scanning system includes a confocal optical imaging system with a laser beam being focused on a small spot on the wafer surface to be scanned. The optics include an objective lens located closest to the wafer with means being provided to vary the spacing of the lens from the wafer over small distances to thus change the focal plane of the system. The wafer may be independently driven in two orthogonal directions in a plane generally perpendicular to the imaging system to bring selected portions thereof into view of the optics. During scanning, the wafer is rapidly vibrated in one of the directions while it is slowly moved in the other direction with a series of digital output signals being provided by the light reflected back from the laser spot on the moving wafer to provide precise information for constructing a three dimensional representation of the surface pattern of the wafer.

25 Claims, 13 Drawing Figures fig_1A fig_2 fig_3 fig_5 fig_6 fig_7 fig_9 fig_10 fig_11

SEMICONDUCTOR WAFER SCANNING SYSTEM

BACKGROUND OF THE INVENTION

1. Field of the Invention

The present invention pertains to systems for scanning surface patterns of semiconductor wafers or the like, and more particularly, it pertains to imaging systems utilizing high resolution microscopes with computer controlled scanning devices to provide detailed and accurate output information for detecting defects or for providing accurate spatial measurments.

2. Description of the Prior Art

In the scanning of semiconductor wafers or the like to detect surface pattern defects, a variety of techniques have been utilized that take advantage of various forms of microscopes, both optical and acoustical, having high degrees of image resolution. In optical imaging systems generally, devices similar to T.V. cameras have been utilized wherein electromagnetic radiation is reflected from a relatively large spot on the wafer and processed through an optical system and photodetector device to provide a multi-intensity image which, either digitally or by analog means, can be recreated on an appropriate output device, such as a CRT.

More recently microscope systems for rapidly scanning specimens at high resolution have become available. One such system utilizes an acoustic microscope with the acoustic lens being mounted on a leaf spring arrangement permitting an electromagnetic vibratory drive to rapidly move the lens in a planar mode at a 50 Hz line scan frequency. The specimen is mounted on x-y tilt stages and is provided with separate x-y slow drives to bring the desired portion of the specimen into the field of view of the acoustic lens. A z-axis drive comprised of a piezoelectric stage drive is also provided on the specimen mounting to adapt the microscope for viewing different surface levels on the specimen.

Another recent semiconductor wafer scanning system utilizes a scanning optical microscope with a confocal imaging system. An image is built up on a T.V.-type display by mechanically scanning the wafer across a focused laser spot.

In scanning devices which use a confocal optical arrangement, sharply focused beams, as for example from a laser source, can be directed through the lens system and concentrated on a very small spot on the specimen, then reflected back through the lens system to a detector. By using this type of optic and by scanning the specimen rapidly in a planar mode, together with suitable electronics connected to the photodetector device, an image can be reconstructed based on the reflected intensity from the small spot as it scans over a segment of the specimen in a series of passes. A scanning microscope utilizing a confocal optical system is shown in U.S. Pat. No. 4,198,571 to Sheppard.

SUMMARY OF THE INVENTION

With the system of the present invention, a confocal optical imaging system is provided which utilizes a source of electromagnetic energy and a lens system for focusing beams on a relatively small spot on the semiconductor wafer. The system inoludes an objective lens located closest to the wafer to which substantially parallel transmitted beams are directed from the source and from which substantially parallel reflected beams are transmitted to a detector. This objective lens can be moved over relatively small distances in the direction of the parallel beams to change the focal place of the imaging system for detecting different surface depth levels on the wafer. The wafer itself is mounted on a mechanical scanner which adapts it for planar movement in at least two different directions. This movement can be carried out with large scale movements so as to readily move into view of the imaging system any given portion of the wafer, or a vibratory drive can be utilized to rapidly scan over a relatively small distance on the wafer while the wafer is moved slowly in a perpendicular direction so as to completely scan a small portion of the wafer. During such scanning movement of the wafer, the reflected beams are sampled in a digital fashion at the detector, and a control system is provided to store a measurable characteristic of the reflected beams for each spaced spot detected on the wafer. While the beam characteristic that is detected will normally be its intensity, it will be appreciated that it is within the scope of the present invention to detect other characteristics such as phase, polarization or wavelength, all of which can provide relevant wafer surface detail information. By operating at different surface levels and while the vibratory drive performs a plurality of successive scans at spaced planar positions, a three dimensional image of the scanned portion of the wafer can be provided by utilizing the stored information in an appropriate output device such as a CRT.

It will be appreciated that the high resolution imaging system of the present invention permits ready measurement of line widths and contact area on the wafers. Also, edge profiles and layer thickness at the edges of the lines can be readily and accurately determined, and the registration of overlays on the surface pattern can be readily checked for any misalignment. Finally, the system can be utilized to detect gross imperfections in the wafer including general wafer flatness as well as scratches, flaking, bridging or other gross defects in the line patterns.

DESCRIPTION OF THE PREFERRED EMBODIMENT

Figure 1:
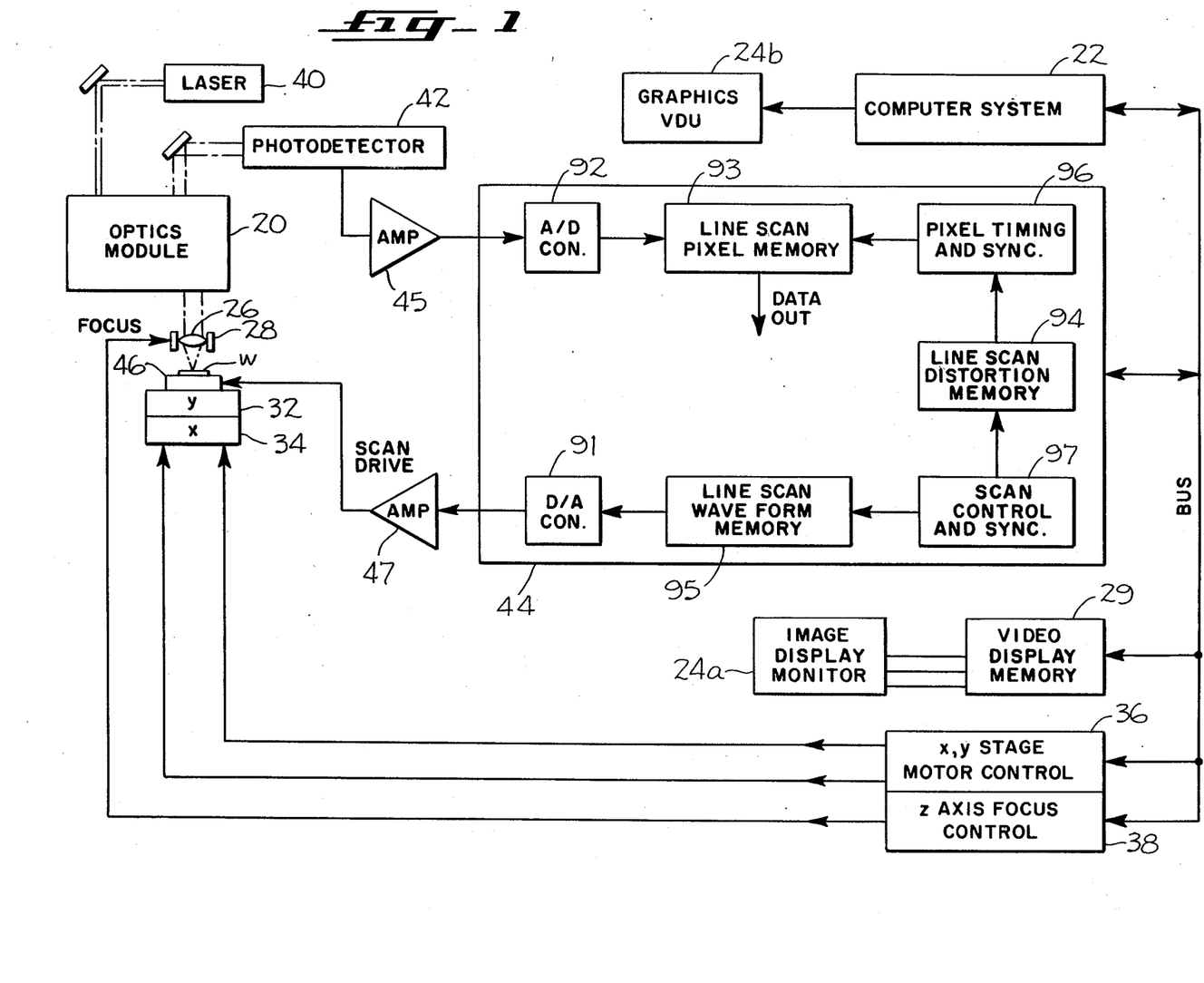
FIG. 1 is a diagrammatic representation of the semiconductor wafer scanning system of the present invention.
Figure 1A:
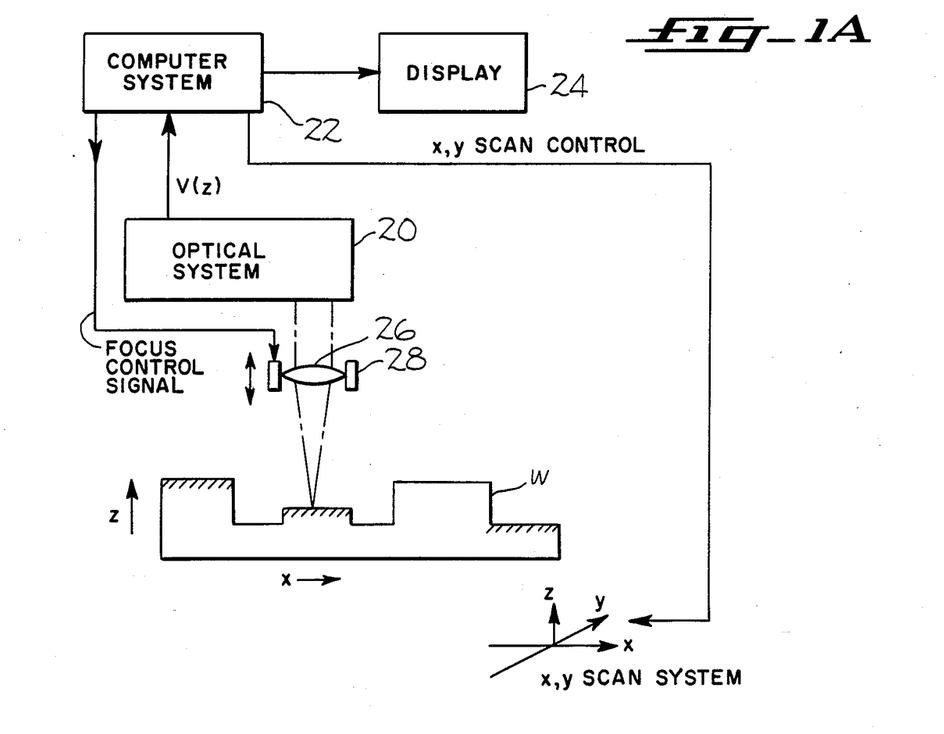
FIG. 1A is a simplified diagrammatic representation of the scanning system of the present invention illustrating a z-x profile of a portion of a wafer as detected by the system.

The basic arrangement of the wafer scanning system of the present invention is schematically shown in FIG. 1A. An optical system 20 is controlled by and provides signals to a computer system 22 which outputs information to various display units 24. The specimen or semiconductor wafer w to be inspected by the system underlies the optical system and is arranged to be moved in a plane lying generally perpendicularly to the projected light beams from the optical system 20. Thus, the wafer is moved in the x and y orthogonal directions by a mechanical scanning mechanism (not shown in FIG. 1A) in a horizontal plane under the control of signals (x, y scan control) from the computer system 22. Movement in the z direction, i.e., in a direction generally parallel to the light beam projected from the optical system, is accomplished by a focus control mechanism 28 which shifts an objective lens 26 (part of the optical system) over very small vertical distances in order to change the focal plane of the optical system. The focus control mechanism is operated from the computer system through a focus control signal to shift the lens 26 up or down. The beam from the optical system is sharply focused with a very narrow depth of field, and it is adapted to be reflected from a surface (if one is present) at the focal plane back through the optical system to a photodector. The signal from the photodetector is digitized by the control circuitry and transmitted to the computer system to represent the intensity of the reflected light from the surface of wafer w as a function of the focus level, z, for separate points in the x-y plane. As indicated by the shading in FIG. 1A, some surfaces at certain z levels will be of relatively low reflectivity while others (the unshaded surfaces) will be of relatively high reflectivity with the differences identifying a changed surface characteristic. Also since the optical system has a very narrow depth of field, reflected intensity peaks at the focal plane and drops off rather sharply as the surface moves away from the focal plane. Thus, the height of the wafer at any particular position thereon can be readily detected by operating the focus control mechanism 28 to achieve a maximum output signal. The computer system tracks the x-y positions of the wafer in conjunction with the z level focal plane position for a given intensity reading and coordinates all of this information in order to provide a three dimensional output representation of the portion of the wafer that is scanned.

An expanded representation of the system of the present invention is shown in FIG. 1 where it can be seen that the computer system 22 is adapted to display information in two separate CRT units including a graphics video display unit 24b (for profiles like the wafer cross-section of FIG. 1A or graphical representation of the data) and image display monitor 24a. In the image display monitor a picture of the wafer portion scanned is recreated out of the stored reflected intensity signals at the various z surface levels for each point in the x-y plane. Such signals are stored in a video display memory 29 during processing and then displayed on the monitor 24a in the desired format.

As shown in FIG. 1 the wafer w is moved in the horizontal plane by x and y stages 34 and 32 respectively which are controlled by x, y stage motor control circuitry 36 under the monitoring of the computer system. As will be explained in greater detail hereinafter, the stages 32, 34 are conventional precision translation tables provided with optical position encoders for sub-micron resolution and accuracy. The motor control circuitry 36 is also conventional in nature providing drive pulses for moving the stages and receiving and processing the signals from the position encoders so as to accurately monitor the position of the wafer at any given instant. The z-axis focus control circuitry 38 provides an output voltage for the focus control mechanism 28 which in the present instance comprises a piezoelectric crystal that expands or contracts in the vertical plane in response to the applied voltage to shift the relative position of lens 26.

As shown diagrammatically in FIG. 1, the optics module containing optical system 20 operates from a laser beam source 40 and provides a sharply focused transmitted beam through the objective lens 26 which is focused on a very small spot (less than 10 microns and, typically, in the sub-micron range) on the wafer w. The reflected beam from the wafer is reflected back through the optics module 20 to a detector 42 comprised of a conventional photomultiplier tube. The control circuitry 44 for the entire system, which will be explained in greater detail hereinafter, is adapted to receive a continuous input light intensity signal from the photomultiplier tube 42 through an amplifier 45 and synchronize this data with the scanner position information. The control circuitry also serves to output a scan drive signal (a sinusoidal waveform) to a vibratory scanning mechanism 46 through an amplifier 47. The scanning mechanism or scanner 46 serves to vibrate the wafer rapidly in the x direction with the stage or linear translator 32 simultaneously moving the wafer slowly in the y direction to provide a two dimensional planar scan, such operation to be explained in greater detail hereinafter.

In the control circuitry 44 it will be seen (FIG. 1) that the scan drive waveform is provided digitally out of a line scan waveform memory 95 and that a D/A converter 91 converts the signal to an analog signal for appropriate amplification by amplifier 47. The memory 95 is addressed by scan control and sync circuitry 97. The incoming analog signal from the photodetector 42 is converted to a digital signal by A/D converter 92.

One of the features of the present system is the fact that the scanning mechanism 46 carrying the wafer will move at a varying linear velocity as the wafer w is scanned, but the timing of the digital signal sampling is such that the recorded and stored digital signal information corresponds to generally uniformly spaced points on the wafer so that a distoration free image of the wafer can be created. In order to accomplish this, a line scan distortion memory 94 is provided to control the timing between the sampling of successive digital signals. The information from memory 94 is utilized by pixel timing and sync circuitry 96 which controls a line scan pixel memory 93 that accepts and stores the digital input signals at the appropriate times. Each input signal corresponds to a pixel which is a representation of a very small area on the wafer with the sampled signal at that time being a measurement of the reflected light from such area.

Figure 2:
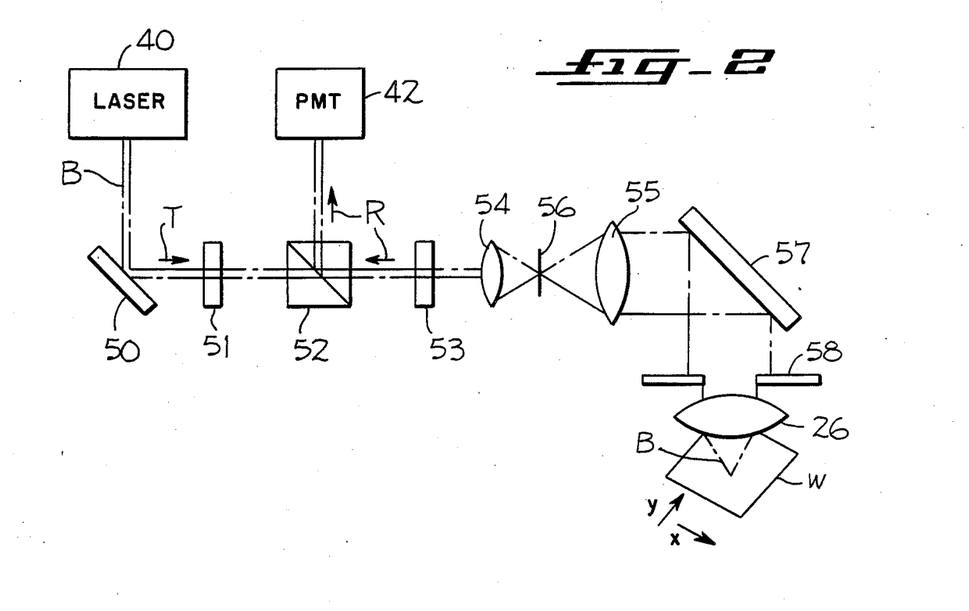
FIG. 2 is a diagrammatic illustration of the optical arrangement of the scanning system of FIG. 1.

The optical system for the apparatus of the present invention is shown schematically in FIG. 2. A laser source 40 provides a closely defined coherent light beam B to a mirror 50 from which the beam is directed through an isolator 51 that allows light to pass only in the direction of the arrow T so as to isolate the laser source from light reflected from the wafer back through the system. A beam splitter 52 is provided allowing a portion of the transmitted beam B from the laser source to pass directly therethrough while reflecting a portion of the return beam in the direction of the arrows R so that it will be received by the photomultiplier tube 42. A optically birefringent plate 53 is provided to control beam polarization in the optical system. In the present system plate 53 is designed as a one-fourth wavelength plate which can be rotated to control the degree of polarization. Objective lenses 54 and 55 receive both the transmitted beam B and the return beam from the wafer and direct them through a spatial filter 56 which has a small pin hole at the focal point of the two lenses. This pin hole must be smaller than the Airy disc of the returning beam, i.e., it must be in the micron diameter range (e.g., 5-10 microns). The objective lens 55 recollimates the transmitted beam B so that only substantially parallel rays of light emanate therefrom, such beam having a diameter of about one centimeter. This beam is reflected by a mirror 57 to change its direction to the vertical, and a controlled aperture device 58 is provided to step down this beam to the desired size. This diameter will be determined by the amount of area desired to be covered by the focused spot on the wafer in a manner to be explained in greater detail hereinafter. Finally, the objective lens 26, which is movable vertically through the focus control mechanism 28, focuses the transmitted beam B on the wafer in a very small spot (typically about one micron in diameter). Scanning is then accomplished as shown by moving the wafer w in the x-y plane so that the laser beam spot will continuously scan across a small portion thereof.

As pointed out, the present optical system comprises a confocal imaging system wherein a beam of light is transmitted through the optical system and focused upon a particular spot on the specimen, and light reflected from the spot forms a return beam which is directed back through the identical optical system. As shown in FIG. 2, the reflected or return light beam will pass back through the objective lenses 26, 55 and 54 and through plate 53. The beam splitter 52 causes a portion of the beam to be directed at right angles (in the direction of arrows R) to the photomultiplier tube 42. The portion of the return light that passes through the beam splitter 52 will be absorbed in the isolator 51 so that it will not interfere with the beam generated by the laser source 40 so as to create false signal information.

Figure 3:
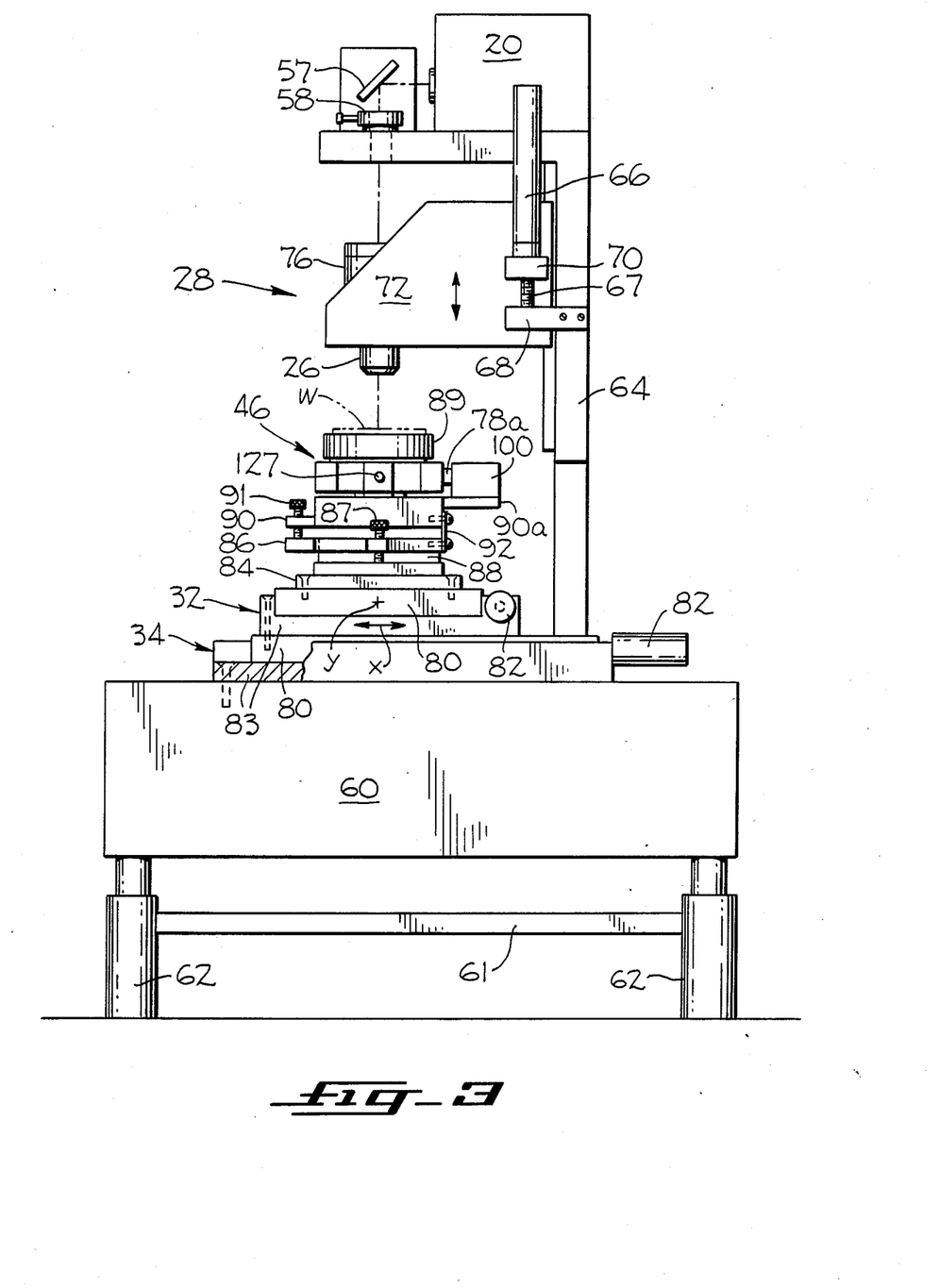
FIG. 3 is a side elevation, partially in section, of the scanning system of the present invention.

The mechanical structure which comprises the semiconductor wafer scanning system of the present invention is shown in FIGS. 3 through 7. Referring first to FIG. 3, it will be seen that the entire wafer drive apparatus and optical system is arranged to be mounted upon a granite surface plate 60 which is seated upon a table 61 and isolated therefrom by four piston and cylinder type air springs 62 mounted to support each corner of the surface plate. A frame structure 64 is elevated above the surface plate 60 to provide support for the optical module 20 and the focus control mechanism 28.

Figure 5:
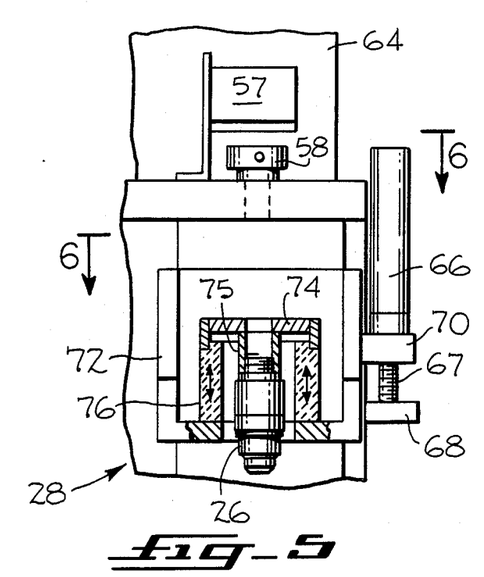
FIG. 5 is a front elevation, partially in section, of the focus control apparatus of the scanning system of FIG. 3.
Figure 6:
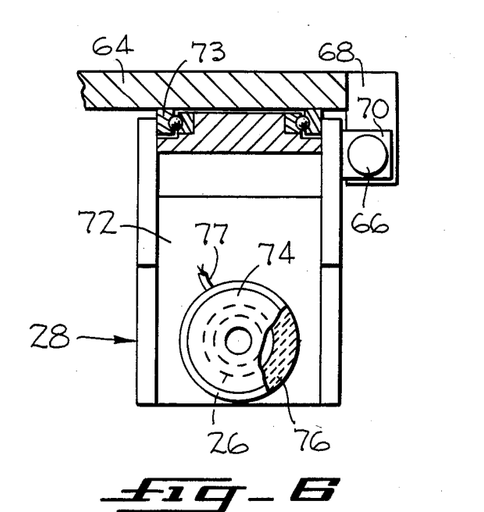
FIG. 6 is a section taken along line 6—6 of FIG. 5.

The details of the focus control mechanism 28 are best shown in FIGS. 3, 5 and 6. The movable objective lens 26 will be seen to be mounted within a cage 72 open at the top and the front and with a back face (FIG. 6) adapted to slide within track 73 on the upright face of the frame 64. A support bracket 70 is attached to one side of cage 72 projecting outwardly therefrom to support a DC servo meter 66 with the projecting lead screw 67 thereof being adapted to engage the upper face of a support bracket 68 secured to the main upright frame 64. It will be seen (from FIG. 3) that movement of the screw 67 within the motor assembly 66 serves to raise or lower the objective lens 26 relative to the underlying wafer support assembly. This lens movement is provided only for gross alignment of the optical system relative to the wafer surface, i.e., to move the optical system in to the basic focal range of the optics. Use of the motor 66 to elevate the lens 26 well above the underlying wafer support structure also permits the wafer to be readily loaded and unloaded.

The fine focusing of the objective lens 26 is accomplished by means of a piezoelectric crystal 76 of generally cylindrical shape (FIGS. 5 and 6) which is attached between the base of the cage 72 and a overhead annular support member 74 which has a central hub 75 to which the upper end of the mount for lens 26 is threaded (FIG. 5). By varying the voltage to the electrical lead 77 (FIG. 6) the crystal 76 may be axially contracted or expanded in the direction of the arrows (FIG. 5) so as to, in turn, lower or elevate the objective lens 26 relative to the underlying wafer. It will be appreciated that the movement of lens 26 during the application of different electrical potentials to crystal 76 will be in the micron or submicron range so that relatively small differences in surface levels on the face of the wafer can be readily detected.

Figure 4:
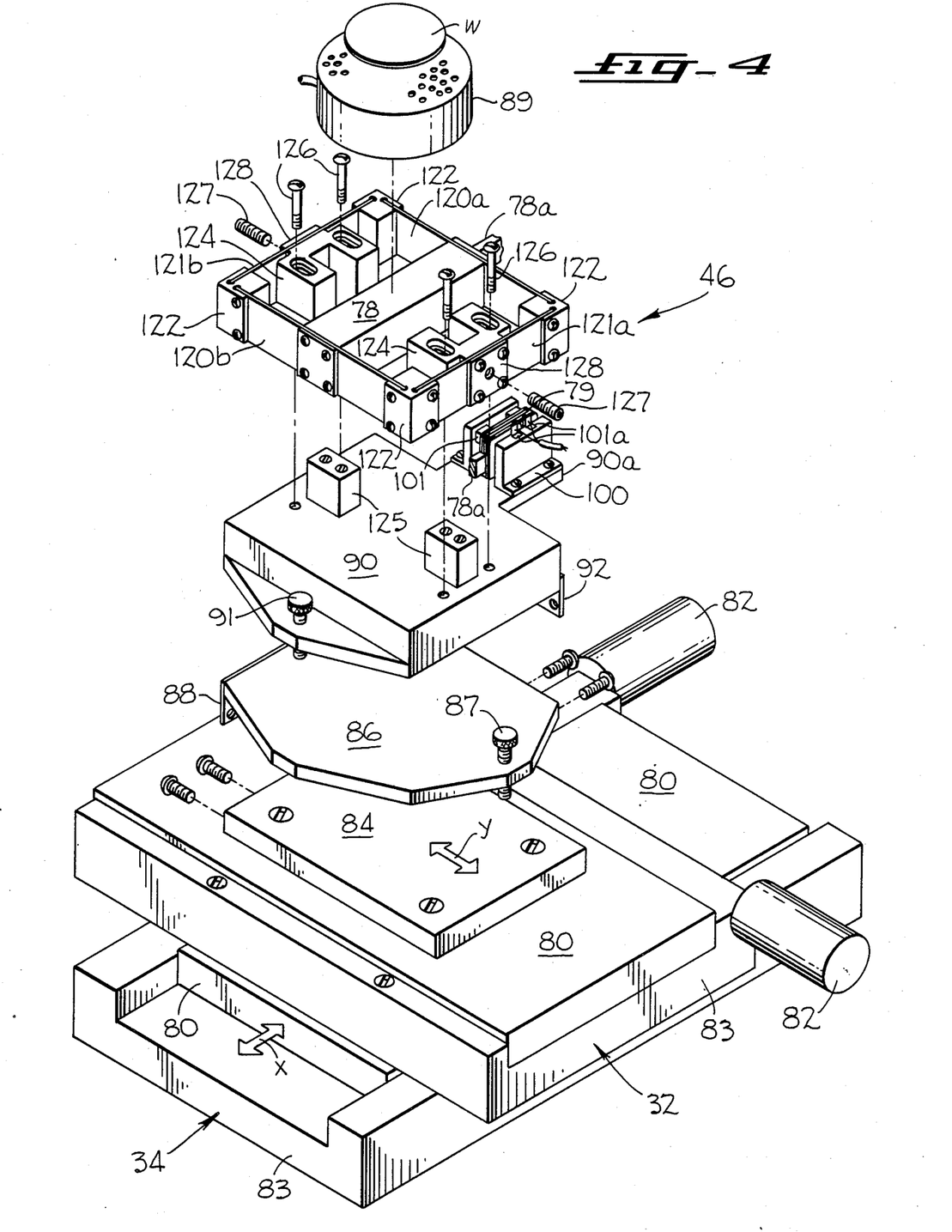
FIG. 4 is an exploded isometric view of the scanner and x-y planar drive mechanism of the system of the present invention.

The planar drive arrangement is best shown in the exploded view of FIG. 4. It will therein be seen that each of the x and y drive devices or stages 34, 32 is comprised of a conventional precision translation table which, in the presently described embodiment of the invention, is designed to have about six to eight inches of linear travel. These tables each include a drive motor 82 which serves to drive a slide block 80 within a channel shaped frame 83 by means of a lead screw (not shown) which is threaded to a nut attached to the slide block 80. Although not shown, it will be appreciated that each translation table includes an optical position encoder therein with submicron resolution and accuracy which serves to feed continuous position signals back to the computer 22 so that the precise position of the wafer in the x-y plane at any given time can be controlled and correlated with the reflected intensity measurements from the optical system during the operation of the apparatus. A flat lower tilt plate 84 is attached to the upper face of slide block 80 of the upper or Y-stage translation table 32, and middle tilt plate 86 is secured thereto by means of a leaf spring 88 which is rigidly bolted to the adjacent spaced ends of both of the tilt plates. Tilt adjusting screw 87 is threaded through the end of tilt plate 86 opposite to the mounting of spring 88 so as to bear against the upper surface of the lower tilt plate 84 so that middle tilt plate (and the structure supported thereabove) can be tilted about the x-axis by adjustment of the screw 87. In a similar manner, an upper tilt plate 90 is secured in spaced relationship to the middle tilt plate 86 by means of a leaf spring 92, bolted to their rearward edges, and a tilt adjusting screw 91 is threaded through the forward edge of tilt plate 90 to bear against the upper surface of tilt plate 86 so as to adjustably rotate the tilt plate 90 about the y-axis. It will be understood that in setting up the apparatus initially and checking it thereafter, it is essential that the tilt screws 87 and 91 are properly adjusted to insure that the surface of upper tilt block 90 lies in a perfectly horizontal plane precisely perpendicular to the path of the light beam from the overhead optical system 20.

Figure 7:
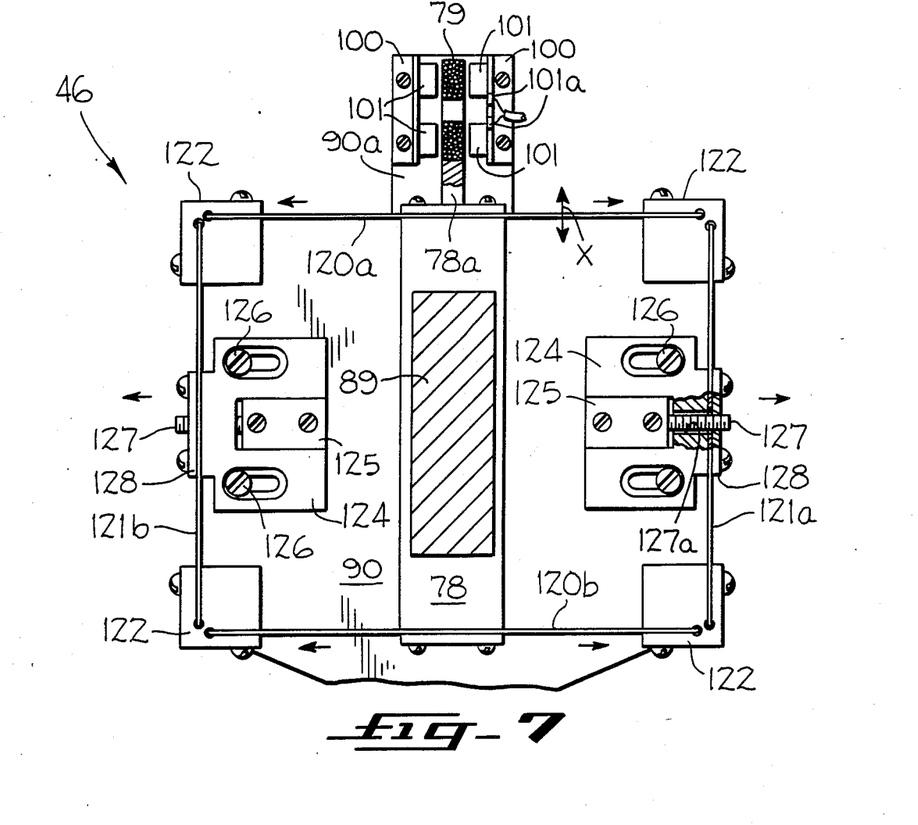
FIG. 7 is a top plan of the vibratory scanning mechanism of the system of the present invention.

The vibratory scanner mechanism 46, by which the wafer w is rapidly vibrated in the direction of the x-axis, is shown in detail in FIG. 7 and the exploded view of FIG. 4. It will be seen that the scanner mechanism comprises a rectangular structure including a pair of leaf springs 120a and 120b for supporting the driving member and a pair of tension adjusting leaf springs 121a and 121b. The springs are arranged in a rectangular structure by attachment to four corner blocks 122 with the ends of each of the leaf springs being tightly clamped to the corner blocks by bolts as shown in FIG. 7. A solid drive bar 78 is firmly attached to and extends between the midpoints of each of the vibratory leaf spring 120a and 120b. Positioned atop the drive bar 78 is a vacuum chuck 89 which is supplied with a vacuum to hold the wafer w securely upon its flat upper surface. The rearwardly projecting end 78a of the drive bar 78 mounts a coil 79 to which a drive current is applied from the control circuitry 44 through amplifier 47 (FIG. 1). A plurality of fixed magnets 101 are mounted upon upright mounting blocks 100 adjacent to the coil 79 so as to complete the electromechanical drive arrangement for the scanner. The mounting blocks 100 are positioned upon and secured to an extension 90a of the upper tilt plate 90, as shown in FIG. 4, and also serve to mount terminals 101a (FIG. 4) through which the coil 79 is connected to the drive circuitry.

In order to secure the scanner 46 to the upper tilt plate 90, U-shaped mounting blocks 124 are bolted to the midpoint of each of the tensioning springs 121a, 121b through attachment plates 128. Each of the attachment plates has a threaded hole in the center thereof for receiving a set screw 127. Each screw extends freely through a passage 127a in its associated U-shaped mounting block 124, as shown in FIG. 7. Abutment blocks 125 are fixedly secured to the upper face of upper tilt plate 90 (FIG. 4) and provide surfaces against which the set screws 127 abut. Each mounting block 124 is also secured upon the upper face of upper tilt plate 90 by means of bolts 126 which, as shown in FIGS. 4 and 7, are received in slots extending through the blocks so that loosening of the bolts permits the blocks to be shifted laterally with respect to the scanner. It will be appreciated that the mounting blocks 124 are thus free to slide upon the lateral faces of the abutment blocks 125 before the bolts 126 are fully tightened thereby permitting the tension springs 121a, 122b to be bowed outwardly in the direction of the arrows from their innermost positions as shown in FIG. 7. This is done in order to apply the proper amount of tension in the leaf springs 120a and 120b so as to adjust the mechanical resonant frequency of the system to that desired. This mechanical resonant frequency should be set just slightly higher than the operating or drive frequency of the system so that the system will be energy efficient but so that the oscillatory drive will never pass through the resonance point wherein loss of control and damage to the structure could occur. It will be seen that by rotating the set screws 127 to move the plates 128 outwardly of the abutment blocks 125, the tensioning springs 121a, 121b bow outwardly to place an axial tensioning force on the springs 120a, 120b in the direction of the arrows shown in FIG. 7. Since each tensioning spring 121a, 121b can be adjusted separately through its associated set screw 127, it will be recognized that this separate adjustment of each side of the spring support system can be used to compensate for any asymmetry in the spring system construction to insure that a perfectly symmetrical drive arrangement is achieved.

With the magnets 101 arranged as shown in FIG. 7, it will be apparent that application of an alternating current to the coil 79 will shift the drive bar 78, and the wafer w supported thereby, backwardly and forwardly in the direction of the arrow X (FIG. 7) at the frequency of the alternating current applied bowing the support springs 120a, 120b accordingly. This lateral movement, which comprises the scan width of the system on the wafer, is set for a typical excursion of about 2 millimeters.

Figures 8, 8A:
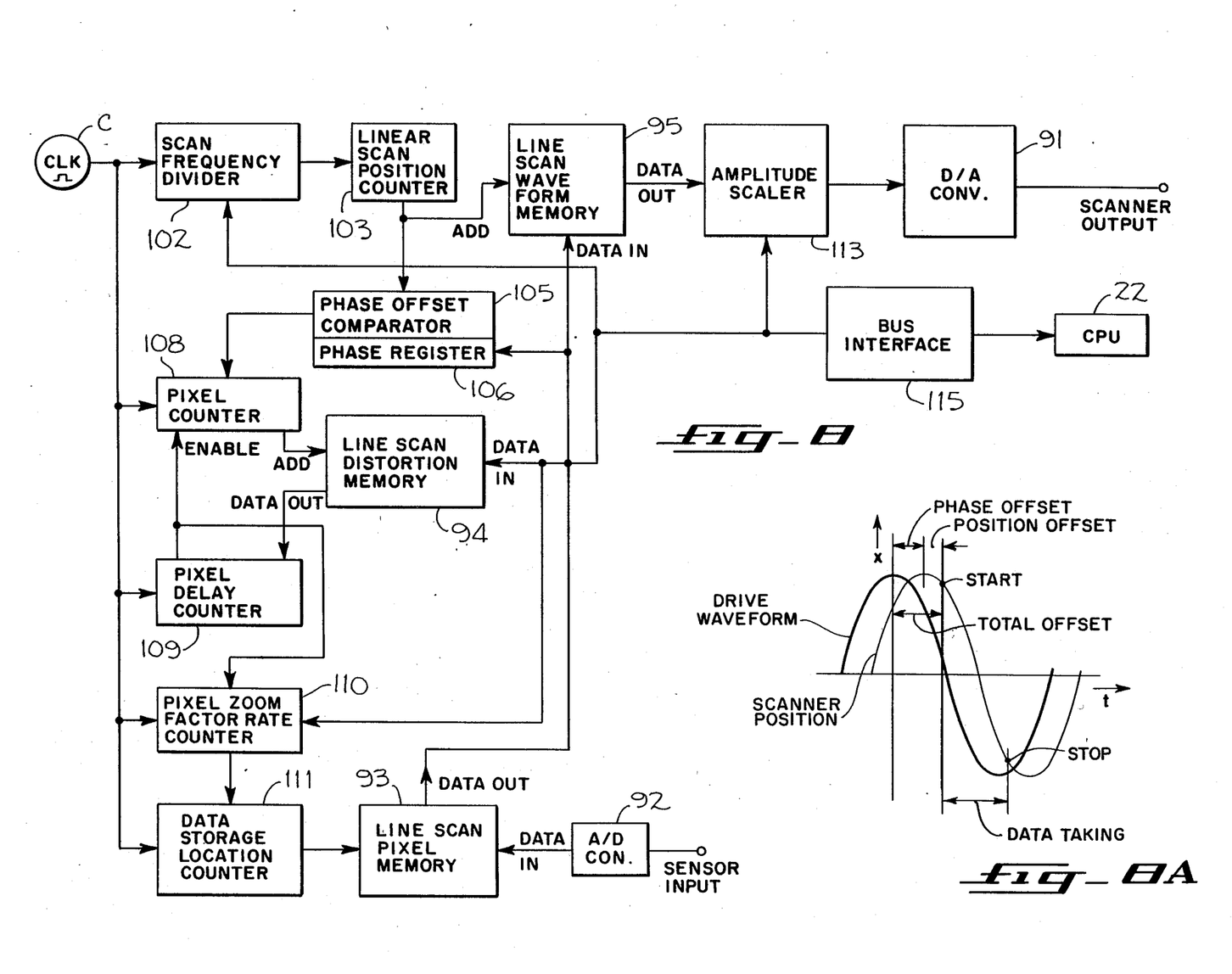
FIG. 8 is a block diagram view of a portion of the control system of the apparatus of the present invention.
FIG. 8A is a schematic representation of the vibratory drive waveforms illustrating the phase relationship between the control signal and the mechanical apparatus.

The control circuitry 44 for the scanning system of the present invention is shown in detail in FIG. 8. It will be seen that the scan control and sync circuitry 97 (FIG. 1), which provides the drive signal to the coil 79, is comprised of a scan frequency divider 102, a linear scan position counter 103, a phase offset comparator 105, and a phase register 106. A clock C provides a pulse train at a suitable frequency as determined by the appropriate number of data points required during each individual scan across the viewed portion of the wafer, the variable delay counts necessary between each data point, and the scanning rate. As an example of the system of the present invention, the clock is arranged to provide pulses at a 10 MHz rate and the scanner 46 is adapted to be sinusoidally driven at a 50 Hertz rate with the sinusoidal wave being broken down into 2048 digital increments in order to achieve the appropriate resolution. Thus, the scan frequency divider circuitry 102 is programmed by the computer 22 to divide the clock frequency down into a 102.4 kHz (50×2048) pulse rate which are counted by the linear scan position counter 103 in 2048 count cycles. Each count is fed into the line scan waveform memory 95 to address the data stored therein, such memory comprising a conventional RAM chip storing the digital data for forming the sine wave. The data is output from the memory in accordance with the sequential incoming signals from the position counter 103. A digital amplitude scaler 113 applies an appropriate programmable scaling factor to the digital data, and D/A converter 91 provides the analog sinusoidal drive current to the coil 79 in the scanner drive system to drive the scanner in the manner previously explained.

Since, as is conventional in vibratory drive systems, there exists a phase difference between the drive waveform and the actual spatial position of the scanner at any given time, this phase difference must be accounted for if the optical imaging system 20 is to accurately correlate the received data with a given wafer location. Thus, phase offset comparator 105 sequentially receives the position signals from the counter 103 and compares them with a digital number set in the phase register 106 that represents the phase offset between the driving waveform and the actual scanner position at any given time. Upon the appropriate comparison, a start or reset signal is transmitted to a pixel counter 108 to initiate the data taking process.

FIG. 8A shows in diagrammatic form the function provided by the aforedescribed circuitry. The sinusoidal electrical drive waveform is shown, and, offset by a phase angle, is a second waveform representing the actual scanner position. Furthermore, since it is undesirable to record imaging data over the full movement of the scanner mechanism in one direction because the slow linear movement at the ends of the stroke would create distortion, an additional offset from the start of movement in the given direction up to the position where the data recording process begins must be accounted for. This additional offset is known as the position offset and is shown in FIG. 8A. Thus, starting from the initiation of one linear tracking movement, i.e., at the peak of the electrical waveform of FIG. 8A, a total offset representing both the phase offset and the position of offset must be accounted for. A number representing the number of counts out of counter 103 to allow for this offset is set into the phase register 106, and the counter 103 starts to count at the peak of the drive wave form. The digital number in the phase offset comparator 105 which is sequentially updated by counter 103 will equal the present digital number in the phase register at the start point indicated in FIG. 8A to send the reset signal to the pixel counter 108 and thereby initiate the data taking process. Data taking will continue until just prior to the full movement of the scanner in the given direction when the stop point, as determined by the pixel counting circuitry, will be reached to terminate the data output signals to the computer.

The pixel timing and synchronization circuitry 96 (FIG. 1) as shown in FIG. 8 includes the pixel counter 108, a pixel delay counter 109, a pixel zoom factor rate divider 110 and a data storage location counter 111. As is conventional in digital imaging systems, a scan across the specimen is broken down into a sequence of one-signal elements or "snapshots" each representing a small area on the specimen, the representations of such areas being referred to as pixels. With the system of the present invention up to 4096 pixels can be utilized in one linear scanning movement. Thus, the pixel counter 108 will count a full 4096 counts after the start or reset pulse from the phase offset comparator 105 adding a count each time a new enable pulse is received from the pixel delay counter 109. Since the velocity of the scanner mechanism in not uniform but will peak in the center of its motion and slow down to zero at the ends of the vibratory movement, it is important that this variation in velocity be accounted for so that the timing of the data signals will directly correspond to a uniform spacing of the pixel representations on the wafer in order to provide a distortion-free image for display. In order to accomplish this, the line scan distortion memory 94 is programmed to store a plurality of delay signal counts representing real time delays between each data signal (i.e., pixel counts) which delay signal counts are dependent upon the particular linear position that the scanner is in at any given time. Thus, the pixel delay counter, which receives direct input pulses from the clock C, receives a delay count signal from memory 94 and counts this down to zero to output the enabling signal to the pixel counter 108. The updating of the count in counter 108 also provides the "add" signal to memory 94 so that the next sequential delay count will be transferred to the delay counter 109 to initiate a new count down sequence.

Since only a limited number of pixels in one line can be displayed on conventional digital image display screens (e.g., 512) a programmable pixel zoom factor rate divider circuit 110 is provided to reduce the 4096 possible pixels to the displayable number (i.e., 512). Thus, the rate divider circuit merely divides the incoming pixel signals down by a factor of 8 so that the data recording occurs every eighth pixel. If greater resolution is desired, this circuit can be programmed to divide by a lesser number or even by unity (i.e., all pixels recorded) with only a portion of the scan being imaged in the output display. The output signal from divider 110 activates data storage location counter 111 which sequentially tracks the various addresses in the line scan pixel memory 93 (comprised of a conventional RAM chip). Each sequential pulse from counter 111 addresses the memory 93 so that it will accept the current digital data input from A/D converter 92 representing the current light intensity reading from the photodetector input 42. The line scan pixel memory stores the data and on command will output the data through the bus interface 115 to the central processing unit or computer 22 in accordance with conventional programming techniques.

Figure 9:
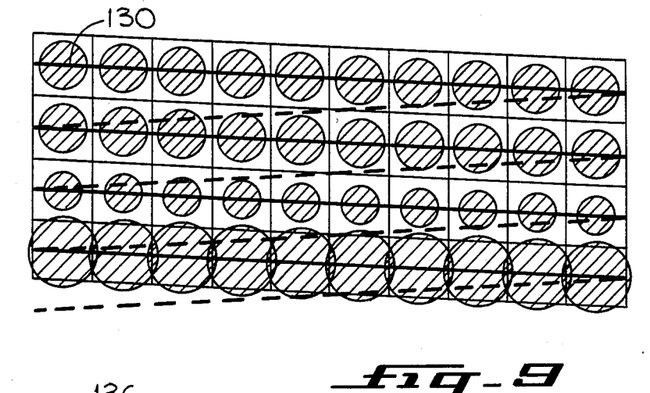
FIG. 9 is a schematic representation of a plurality of successive scanning movements across a portion of a semiconductor wafer illustrating the imaginary pixels which represent tiny wafer areas with respect to which the information is obtained and the laser beam spots from which the reflected intensity measurements are taken.

FIG. 9 shows in diagrammatic form four traces across a portion of a wafer by the scanning system of the present invention. While only ten pixels are indicated for illustrative purposes as comprising one full sweep across the wafer portion, it will be recognized that a great many additional pixels will typically be needed in order to obtain appropriate resolution. Thus, in the system of the present invention, 512 pixels will comprise one sweep of the scanner mechanism 46. The heavy line 130 of FIG. 9 represents the center line of the imaging spot on the wafer as the wafer is moved beneath it. The solid portion of line 130 indicates that portion of the scan when the data recording sequence is "on" while the dashed line portion indicates the position of the wafer while the data recording sequence of "off". It will be recognized that in FIG. 9 there is no "position offset" as previously described so that the scanner records data across its full sweep in one direction from one edge to the other and is "off" as it moves in the opposite direction.

It is important to note from FIG. 9 that the slow movement of the wafer in the Y direction (by stage 32) is such that the return trace of the scanning mechanism brings the scanning spot back to a position whereby the pixels are contiguous not only in the direction of the scanning movement but in the direction perpendicular thereto so as to provide a distortion free image when the data representing each of the pixels is subsequently displayed as a two dimensional image of the wafer surface. As explained previously the distortion correction circuitry of FIG. 8 operates so that the timing of the data taking across the wafer will be adjusted so that the images will be correctly represented as uniformly spaced positions on the wafer as shown. The shaded circles occupying each pixel represent the size of the laser beam spots on the wafer at the time that the intensity signal therefrom is recorded. It will be seen that the first two rows represent a spot size which generally occupies the major portion of each of the pixel areas extending from a position near all four edges thereof. This is an appropriate desired size wherein the diameter of the spot occupies the approximate diameter of the pixel and the apperture control mechanism 58 (FIG. 3) can be adjusted so as to achieve this spot size. The third row indicates a condition wherein the spot size is reduced relative to the pixel size. This will be appropriate so long as the wafer features are coarser then the pixel spacing. The bottom trace indicates a condition wherein the spots overlap slightly the adjacent pixels. Again, this will be appropriate and can be utilized in achieving accurate representation of the wafer surface patterns depending upon the resolution of the system.

Figure 10:
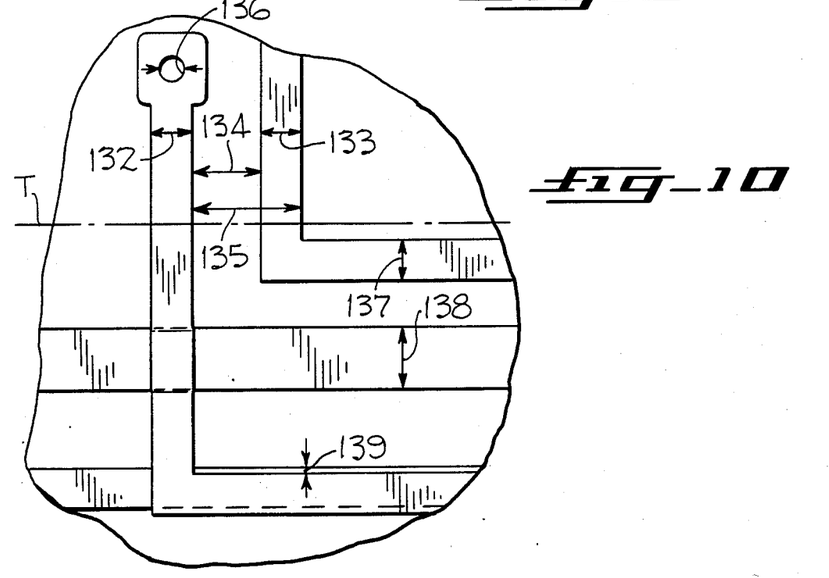
FIG. 10 is an illustration of a portion of a typical semiconductor wafer showing critical dimensions to be measured with the system of the present invention.
Figure 11:
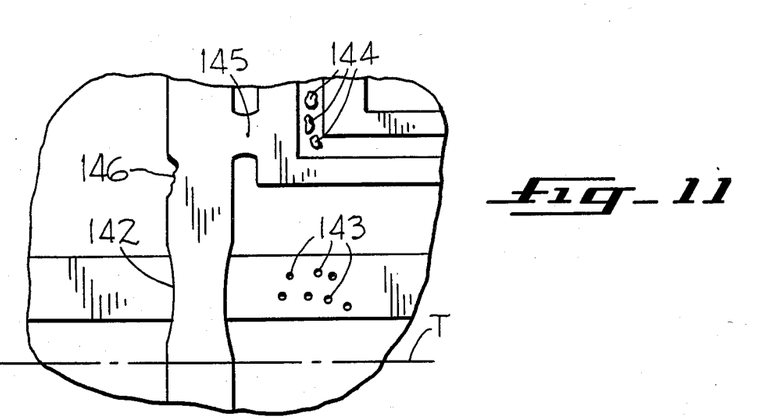
FIG. 11 is an illustration of a portion of a typical semiconductor wafer showing typical defects to be detected with the system of the present invention.

FIGS. 10 and 11 illustrate typical measurements to be made (FIG. 10) and defects to be detected (FIG. 11) in wafer surface patterns utilizing the system of the present invention. Thus, in FIG. 10, with the scanner moving generally in the x direction as represented by trace T, line width measurements of the conductive lines can readily be made as the scanner moves thereacross, as indicated at 132 and 133, it being recognized that the change in elevation at the edges of the lines will readily be detected as a sharp change in reflected intensity at a given depth level. Also, spacing between lines (134) and line offset (135) can also readily be measured. The diameter of a contact hole (136) at the end of a line can also be measured in a similar manner. Due to the fact that the pixels are contiguous both in the x and y directions, it will also be apparent that the stored line-by-line data will permit line measurements to be made at right angles to the trace T also, as at 137 and 138. Finally, the offset of overlaid lines can be detected as at 139.

In FIG. 11 typical defects in wafer surface patterns are found which the system of the present invention can be designed to recognize and display. For example, successive scans in the direction of trace T will indicate where the line width of one conductor may vary due to its proximity to another conductor, as seen at 142, by comparing the data line-by-line. Also, assuming proper resolution, "pinholes" 143 will be indicated by the changes in signal strength as the trace T scans across the wafer, and, in a similar manner, the existance of tiny residues ("scumming") (144), will be detected. Bridging between lines, as at 145, will be detected, as will "rat bite" 146 or other line surface irregularities by comparing the stored data on a line-by-line basis.

Although the best mode contemplated for carrying out the present invention has been herein shown and described, it will be apparent that modification and variation may be made without departing from what is regarded to be the subject matter of the invention.

We claim:

1. A system for scanning semiconductor wafers or the like for determining surface pattern information including means for mounting a wafer for planar motion in at least two orthogonal directions, a source of electromagnetic energy, a confocal imaging system for directing beams of electromagnetic energy from said source to a relatively small spot on said wafer and for receiving reflected beams from said spot on said wafer, said imaging system including an objective lens located closest to said wafer to which substantially parallel beams of electromagnetic energy are directed and from which substantially parallel reflected beams of energy are transmitted, means for moving said wafer over relatively large distances in said directions in order to bring selected portions thereof into view of said imaging system, vibratory means separate from said last named means for moving said wafer rapidly over relatively small distances in one of said directions, means operative in conjunction with said vibratory means for moving the wafer at a relatively slow speed in the other of said directions, means for moving said objective lens over relatively small distances in a direction perpendicular to the plane of said orthogonal directions to change the focal plane of the imaging system for detecting different surface depth levels on said wafer, a detector for receiving said reflected beams from said imaging system and for providing an output signal indicative of a measurable characteristic of the reflected beams from a particular position of the directed beams on said wafer, and control means for providing a three dimensional image of at least a portion of the surface of said wafer by storing a plurality of said output signals during each vibratory movement of said wafer at different depth levels on said wafer surface and at different positions in the other of said directions.

2. A system for scanning semiconductor wafers or the like according to claim 1 wherein said source of electromagnetic energy comprises a laser beam generator.

3. A system for scanning semiconductor wafers or the like according to claim 1 wherein said vibratory means comprises a pair of leaf springs arranged in parallel, a rigid mounting block secured to each of said springs between the end points thereof bridging the gap between the springs, said means for mounting the wafer being secured to said mounting block, and electromagnetic drive means connected to said mounting block to oscillate it along its axis in a direction perpendicular to said springs.

4. A system for scanning semiconductor wafers or the like according to claim 3 wherein each end of each leaf spring is secured to a corner block, said corner blocks at the adjacent ends of the leaf springs being connected together by a tension spring so as to form a generally rectangular structure capable of flexing in the middle along the axis of the mounting block when the mounting block is oscillated.

5. A system for scanning semiconductor wafers or the like according to claim 3 wherein said control means includes means for compensating for the sinusoidal oscillatory motion of the vibratory drive means to provide spacing of said output signals in accordance with a generally uniform spacing of the associated particular positions on said wafer.

6. A system for scanning semiconductor wafers or the like according to claim 1 wherein said means for moving said objective lens comprises a piezoelectric crystal secured to said objective lens, and means for varying the voltage applied to said crystal to cause it to expand or contract and thereby shift the spatial position of said objective lens.

7. A system for scanning semiconductor wafers or the like according to claim 1 wherein the source of energy is a sharply defined light beam and wherein an output signal represents the intensity of the reflected light beam from a spot on said wafer, said spot having a size in the order of 10 microns or less.

8. A system for scanning semiconductor wafers or the like according to claim 7 including means for adjusting said spot size so that the spot size can be generally of a diameter equivalent to the distance through which the wafer is moved between output signals.

9. A system for scanning semiconductor wafers or the like according to claim 7 wherein each vibratory movement in a given direction is divided into a plurality of discrete contiguous segments with the spots occupying a significant portion of each segment, said means for moving the wafer at a relatively slow speed being operative to move said wafer so that said segments are contiguous in the direction transverse to said direction of vibratory movement also, said control means including means for outputing said image of said portion of the wafer by displaying each segment as part of an array as represented by the magnitude of the output signal for the spot associated with that segment.

10. A system for scanning semiconductor wafers or the like according to claim 1 wherein said output signals are provided by sampling at predetermined time intervals and wherein said control means includes means for time compensating for nonconstant velocity movement of said beams on said wafer so that the time spacing of said output signals corresponds to generally uniform dimensional spacing of the sampled spots on the wafer.

11. A system for scanning semiconductor wafers or the like according to claim 10 wherein said time compensating means comprises means for storing a number of predetermined time delay signals, means for sequentially calling up said time delay signals, and means for counting between output signals in accordance with the particular time delay signal called up.

12. A system for optically scanning semiconductor wafers or the like for determining surface pattern information including means for mounting a wafer for planar motion in at least two different directions, means for moving said wafer in said planar directions, a light source, a photodetector, an optical confocal imaging system arranged to receive light beams from said source and direct said beams to a small spot on said wafer in the order of about 10 microns or less and to receive reflected beams from said spot and direct them to said photodetector, said system including a pinhole of a size in the order of said spot size for directing both the transmitted beam to the wafer and the reflected beam to the photodetector, said microscope including an objective lens located closest to said wafer to which substantially parallel beams of light are provided from said source and from which substantially parallel reflected beams of light are transmitted from said wafer, means for moving said objective lens over relatively small distances in the direction of said substantially parallel beams to change the focal plane of said microscope for detecting different surface depth levels on said wafer, means connected to said photodetector for providing an output signal indicative of a measurable characteristic of the reflected light at said spot on the wafer, sampling means for providing a plurality of spaced output signals as said wafer is moved in said planar directions representative of the reflected light characteristics of a plurality of spaced spots on said wafer, and control means for storing the output signals for said plurality of spots as said wafer is moved in said planar directions and as the focal plane of the microscope is changed in order to provide a three dimensional representation of at least a portion of said wafer.

13. A system for optically scanning semiconductor wafers or the like according to claim 12 wherein said light source comprises a laser beam generator.

14. A system for optically scanning semiconductor wafers or the like according to claim 12 wherein said means for moving said objective lens comprises a piezoelectric crystal secured to said objective lens, and means for varying the voltage applied to said crystal to cause it to expand or contract and thereby shift the spacial position of said objecive lens.

15. A system for optically scanning semiconductor wafers or the like according to claim 12 including means for adjusting said spot size so that the spot size can be generally of a diameter equivalent to the distance through which the wafer is moved between output signals.

16. A system for scanning semiconductor wafers or the like for determining surface pattern information including means for mounting a wafer for planar motion in at least two orthogonal directions, a source of electromagnetic energy, a confocal optical imaging system for directing beams of electromagnetic energy from said source to a relatively small spot on said wafer in the order of about 10 microns or less and for receiving reflected beams from said spot on said wafer, means for moving said wafer over relatively large distances in said directions in order to bring selected portions thereof into view of said imaging system, vibratory means separate from said last named means for moving said wafer rapidly over relatively small distances in one of said directions, means operative in conjuction with said vibratory means for moving the wafer at a relatively slow speed in the other of said directions, a detector for receiving said reflected beams for said imaging system and for providing an output signal indicative of a measurable characteristic of the reflected beams from the particular spot position on said wafer, means for storing a plurality of said output signals representing closely spaced spots during each vibratory movement of said wafer in a given direction, and means for providing an image of at least a portion of the surface of the wafer by displaying said stored signals accumulated over a plurality of consecutive vibratory movements.

17. A system for scanning semiconductor wafers or the like according to claim 16 wherein said vibratory means comprises a pair of leaf springs arranged in parallel, a rigid mounting block secured to each of said springs between the end points thereof bridging the gap between the springs, said means for mounting the wafer being secured to said mounting block, and electromagnetic drive means connected to said mounting block to oscillate it along its axis in a direction perpendicular to said springs.

18. A system for scanning semiconductor wafers or the like according to claim 17 wherein each end of each leaf spring is secured to a corner block, said corner blocks at the adjacent ends of the leaf springs being connected together by a tension spring so as to form a generally rectangular structure capable of flexing in the middle along the axis of the mounting block when the mounting block is oscillated.

19. A system for scanning semiconductor wafers or the like according to claim 17 wherein said control means includes means for compensating for the sinusoidal oscillatory motion of the vibratory drive means to provide spacing of said output signals in accordance with a generally uniform spacing of the associated spots on said wafer.

20. A system for scanning semiconductor wafers or the like according to claim 16 including means for adjusting said spot size so that the spot size can be generally of a diameter equivalent to the distance through which the wafer is moved between output signals.

21. A system for scanning semiconductor wafers or the like according to claim 16 wherein each vibratory movement in a given direction is divided into a plurality of discrete contiguous segments with the spots occupying a significant portion of each segment, said means for moving the wafer at a relatively slow speed being operative to move said wafer so that said segments are contiguous in the direction transverse to said direction of vibratory movement also, said control means including means for outputing said image of said portion of the wafer by displaying each segment as part of an array as represented by the magnitude of the intensity of the output signal for the spot associated with that segment.

22. A system for scanning semiconductor wafers or the like according to claim 16 wherein said output signals are provided by sampling at predetermined time intervals and wherein said control means includes means for time compensating for nonconstant velocity movement of said beams on said wafer so that the time spacing of said output signals corresponds to generally uniform dimensional spacing of the spots on the wafer.

23. A system for scanning semiconductor wafers or the like according to claim 22 wherein said time compensating means comprises means for storing a number of predetermined time delay signals, means for sequentially calling up said time delay signals, and means for counting between output signals in accordance with the particular time delay signals called up.

24. A process for scanning semiconductor wafers or the like for determining surface pattern information comprising placing a wafer on a mounting block and moving the wafer in a plane to bring a particular portion thereof into the view of an overhead optical imaging system, rapidly oscillating the wafer in one direction while slowly moving it in an orthogonal direction in said plane, directing a small beam of light from said imaging system to a spot in the order of 10 microns or less on said wafer during said oscillatory movment and permitting it to be reflected back through said system to a detector thereby causing the system to scan said portion of the wafer during said movement, digitally recording the reflected beam information of the spot at closely spaced positions along parallel scan lines on said wafer during said oscillatory movement, changing the focal plane of the imaging system to cause the spot to be focused at different levels on said wafer surface while repeating said oscillatory movement, and displaying a three dimensional representation of said portion of the wafer surface based on said recorded reflected beam information.

25. A process according to claim 24 wherein the beam positions at which the reflected beam information is recorded are generally uniformly spaced on the wafer, and including adjusting the timing between the recording of beam information in accordance with the changing velocity of movement of the wafer in order to obtain said generally uniform spacing of the beam positions on the wafer.

* * * * *